US00PP35380P3

(12) United States Plant Patent
Baasch

(10) Patent No.: US PP35,380 P3
(45) Date of Patent: Sep. 12, 2023

(54) ***CANNABIS* PLANT NAMED 'DKJ127'**

(50) Latin Name: ***Cannabis sativa* (L.)**
Varietal Denomination: DKJ127

(71) Applicant: Vertanical GmbH, Gräfelfing (DE)

(72) Inventor: Bastian Baasch, Utting am Ammersee (DE)

(73) Assignee: Vertanical GmbH, Gräfelfing (DE)

( * ) Notice: Subject to any disclaimer, the term of this patent is extended or adjusted under 35 U.S.C. 154(b) by 0 days.

(21) Appl. No.: 17/803,816

(22) Filed: Dec. 8, 2022

(65) Prior Publication Data

US 2023/0189677 P1 Jun. 15, 2023

(30) Foreign Application Priority Data

Dec. 9, 2021 (QZ) ..... PBR 2021/3223

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
See application file for complete search history.

*Primary Examiner* — Susan McCormick Ewoldt
(74) *Attorney, Agent, or Firm* — Myers Bigel, P.A.

(57) ABSTRACT

'DKJ127' is a *Cannabis sativa* cultivar suitable for production of herbal medicinal products (standardized extract) having high to very high THC content, about 17-20% THC eq.

14 Drawing Sheets

Latin name of the genus and species: The Latin name of the novel plant cultivar disclosed herein is *Cannabis sativa* (L.).

Variety denomination: This new and distinct cultivar of *Cannabis saliva* (L.) has been given the denomination 'DKJ127'.

STATEMENT OF PRIORITY

This application claims the benefit, under 35 U.S.C. § 119 (a-c), of European Community Plant Variety Application No. 2021/3223 filed on Dec. 9, 2021, the entire contents of which is incorporated by reference herein.

BACKGROUND OF THE INVENTION

*Cannabis sativa* is indigenous to Central Asia, and South Asia and has long been used for fiber (hemp), seed and seed oils, for medicinal purposes, and as a recreational drug. The present invention is directed to a new and distinct *Cannabis sativa* cultivar named 'DKJ127' having a high level of THC, a low degree of variation in chemical profile and low susceptibility to diseases, and which is suitable for further processing into a standardized medicinal product.

Lineage, Cultivation, and Selection.

A parental "motherplant" for 'DKJ127' was originally selected from seed of the *Cannabis* strain 'Jack Herer' using phenotype selection. Due to its complex lineage, seed of the 'Jack Herer' strain is known to display many different phenotypes and does not produce uniform plants. Therefore, phenotype selection was initiated to develop a suitable parental motherplant having the desirable phenotype, which was then further propagated via cuttings to show that the characteristics of the selected candidate variety as described are stable over different propagation generations.

For selection of the variety 'DKJ127', two hundred 'Jack Herer' seeds were individually grown under unique cultivation/environmental conditions (see, Table 1), and a stock of motherplants was created by taking cuttings from the plants grown from each of the 200 'Jack Herer' seeds. The selection criteria for the specific genetics and phenotypes of the seed grown plants included the successful germination of the seed (must germinate), successful cultivation of the motherplant through the vegetative and flowering phases, the rooting behaviour of cuttings (successful rooting), yield (flower size), the resistance to diseases, such as grey mould, and a tetrahydrocannabinolic acid (THCA) content of at least 15%.

The motherplants start as cuttings in 4×4 cm rockwool cubes, which are then transplanted three weeks later into 20×20 cm rockwool cubes. The lifetime of a motherplant is between 8 and 12 months, after which it is discarded. During its lifetime, a motherplant can deliver cuttings every second week, starting from week 8 of its life. Every time after taking cuttings, the motherplants are trimmed and shaped. Cuttings are grown in an 18-hour day light cycle with a 6-hour night period. Total time in vegetative stage is 2 weeks.

To induce flowering, the period of light is shortened to 12 h/day and the nutrient recipe is switched to a higher potassium and phosphorus blend to promote development of the flowers. The plants are pruned about 10 days after starting induction for flowering. Pruning removes unnecessary leaves and branches from the lower side of the plant to allow light to reach all flowers. The period of flowering stage for DKJ127 is about 9 weeks after which flowers are harvested. Starting from 30-40 cm height, the plants can reach up to 140 cm-150 cm in height, at the end of the flowering stage.

As part of the selection process, batch-to-batch consistency was analyzed based on the cannabinoid and terpene profile. 'DKJ127' contains THCA at a content of approximately 18% and this high level of THCA was observed batch to batch for 'DKJ127'. Only small amounts of other cannabinoids are present in 'DK-J127', mainly Cannabigerol (CBG) and Cannabidiol (CBD) at a content of about 0.7% and 0.2%. No other cannabinoids are present in 'DKJ127' in significant amounts. The major terpenes found in 'DK-J127' include alpha-pinene, camphene, beta-pinene, beta-myrcene, d-limonene, linalool, beta-caryophyllene, alpha-humulene, nerolidol, guaiol, and alpha-bisabolol.

Environmental conditions:

TABLE 1

Environmental Conditions Cultivation Phases

| Phase/ Parameter | AIR-temperature (° C.) | AIR-Rel. Humidity (%) | AIR-CO2 Level (ppm) | LIGHT-daylength (hours) |
|---|---|---|---|---|
| Rooting Phase | 25-29 | n/a | 500-800 | 18 |
| Vegetative Phase | 22-28 | 60-80 | 500-800 | 18 |
| Flowering Phase | 22-28 | 30-50 | 500-1000 | 12 |

Table 2 and Table 3 below provide data used in the selection process.

TABLE 2

THCA and percent weight loss on drying of 22 selected strains

| Strain-ID | Loss on drying % (w/w) | THCA |
|---|---|---|
| DK-J120-000 | 5% | 23.80% |
| DK-J127-000 | 5% | 21.70% |
| DK-J019-000 | 5% | 21.60% |
| DK-J115-000 | 6% | 20.50% |
| DK-J064-000 | 5% | 20.30% |
| DK-J087-000 | 5% | 20.10% |
| DK-J002-000 | 5% | 19.60% |
| DK-J186-000 | 5% | 19.10% |
| DK-J140-000 | 5% | 18.20% |
| DK-J168-000 | 6% | 17.90% |
| DK-J176-000 | 5% | 17.90% |
| DK-J149-000 | 5% | 17.80% |
| DK-J105-000 | 6% | 17.60% |
| DK-J187-000 | 6% | 17.50% |
| DK-J039-000 | 7% | 17.40% |
| DK-J166-000 | 6% | 17.20% |
| DK-J093-000 | 6% | 16.80% |
| DK-J024-000 | 6% | 16.60% |
| DK-J085-000 | 7% | 16.50% |
| DK-J110-000 | 5% | 16.50% |
| DK-J033-000 | 5% | 15.70% |
| DK-J099-000 | 7% | 12.40% |

TABLE 3

Yield and cultivation behaviour and THC content

| Strain-ID | ht [cm] | wt wet [g] | wt dry [g] | Factor | seeds in flowers | maturity level [1-10] |
|---|---|---|---|---|---|---|
| DK-J002 | 155 | 260 | 60.25 | 4.3 | no | 8 |
| DK-J003 | 175 | 600 | 133.2 | 4.5 | no | 9 |
| DK-J019 | 165 | 440 | 74.8 | 5.9 | no | 7 |

TABLE 3-continued

Yield and cultivation behaviour and THC content

| | | | | | | |
|---|---|---|---|---|---|---|
| DK-J024 | 176 | 740 | 142.35 | 5.2 | no | 8 |
| DK-J033 | 180 | 480 | 105 | 4.6 | no | 7 |
| DK-J039 | 180 | 1460 | 369.92 | 3.9 | yes | 8 |
| DK-J064 | 200 | 860 | 193.6 | 4.4 | no | 9 |
| DK-J085 | 165 | 620 | 136.8 | 4.5 | no | 8 |
| DK-J087 | 175 | 580 | 131.89 | 4.4 | no | 9 |
| DK-J088 | 150 | 220 | 43.63 | 5.0 | no | 7 |
| DK-J093 | 155 | 2000 | 417.31 | 4.8 | no | 7 |
| DK-J099 | 170 | 500 | 107.79 | 4.6 | no | 7 |
| DK-J105 | 170 | 1040 | 216.14 | 4.8 | no | 8 |
| DK-J110 | 130 | 1220 | 205.13 | 5.9 | no | 7 |
| DK-J115 | 200 | 1020 | 212.83 | 4.8 | no | 9 |
| DK-J127 | 180 | 840 | 193.27 | 4.3 | no | 9 |
| DK-J130 | 160 | 1120 | 214.79 | 5.2 | no | 7 |
| DK-J140 | 170 | 620 | 146.22 | 4.2 | no | 8 |
| DK-J149 | 200 | 840 | 186.4 | 4.5 | no | 7 |
| DK-J166 | 180 | 420 | 98.35 | 4.3 | no | 8 |
| DK-J186 | 184 | 1120 | 236.56 | 4.7 | no | 8 |
| DK-J187 | 185 | 1060 | 286.38 | 3.7 | no | 8 |

| Strain-ID | disease | rooting time | rooting test 1 [20] | rooting test 2 [11] | THC eq. [%] |
|---|---|---|---|---|---|
| DK-J002 | no | 10-18 days | 20 | 11 | 19.6% |
| DK-J003 | no | 10-18 days | 20 | 10 | NA |
| DK-J019 | no | 10-18 days | 19 | 11 | 21.6% |
| DK-J024 | no | 10-18 days | 6 | 7 | 16.6% |
| DK-J033 | no | 10-18 days | 20 | 11 | 15.7% |
| DK-J039 | no | 10-18 days | 17 | 11 | 17.4% |
| DK-J064 | no | 10-18 days | 20 | 11 | 20.3% |
| DK-J085 | no | 10-18 days | 20 | 11 | 16.5% |
| DK-J087 | no | 10-18 days | 20 | 11 | 20.1% |
| DK-J088 | no | 10-18 days | 6 | 11 | NA |
| DK-J093 | no | 10-18 days | 5 | 11 | 16.8% |
| DK-J099 | no | 10-18 days | 20 | 11 | 12.4% |
| DK-J105 | no | 10-18 days | 20 | 11 | 17.6% |
| DK-J110 | no | 10-18 days | 10 | 11 | 16.5% |
| DK-J115 | no | 10-18 days | 20 | 11 | 20.5% |
| DK-J127 | no | 10-18 days | 19 | 11 | 21.7% |
| DK-J130 | grey mould | 10-18 days | 10 | 11 | NA |

TABLE 3-continued

| Yield and cultivation behaviour and THC content | | | | | |
|---|---|---|---|---|---|
| DK-J140 | no | 10-18 days | 20 | 11 | 18.2% |
| DK-J149 | no | 10-18 days | 5 | 11 | 17.8% |
| DK-J166 | no | 10-18 days | 20 | 11 | 17.2% |
| DK-J186 | no | 10-18 days | 20 | 11 | 19.1% |
| DK-J187 | no | 10-18 days | 10 | 11 | 17.5% |

In summary, out of 200 'Jack Herer' seedlings, 22 were selected for further analysis and asexual reproduction via cuttings. These 22 phenotypes were brought into the flowering phase and material of those was dried and analyzed for THCA content. The content of THCA, terpene profile and odour were included as criteria in the selection of the line named J127 (DK-J127-000) ('DKJ127'). Thus, from an initial group of 200 'Jack Herer' seedlings, exhibiting a wide range of phenotypes, a single strain, 'DKJ127', having the desired and true to type characteristics as described herein was selected.

Although 'Jack Herer', due to its complex lineage, is known to be a strain that displays many different phenotypes, the applicant has now developed a plant that shows stability over multiple propagation generations.

The detailed steps of cultivation and conditions for the initial motherplants from seeds is described as follows:

Two hundred 'Jack Herer' seeds were individually grown under unique cultivation conditions and motherplants were created.

Step 1: Preparation of rockwool cubes (4.0×4.0×4.0 cm) with tap water.

Step 2: Transplantation of seed onto the rockwool cube.

Step 3: Seed covered by rockwool, about 1 cm deep.

Step 4: Rockwool cube placed under a white plastic foil tent.

Step 5: Seed germinates after 3-14 days underneath the white plastic foil tent.

Step 6: Evaluation of whether the selection criteria have been met.

Step 7: Transplantation of seedling in rockwool cubes (20×20×20 cm).

Step 8: Soaking with Fertilizer with EC 0.5-3.5 and pH value of 4.5-7.

Step 9: Cultivation period of plants before initial propagation by taking cuttings is 3-6 weeks.

Step 10: Plants are kept in same conditions with daily watering and increase of light intensity up to specifications for plants in Vegetative Phase.

The detailed steps of cultivation of motherplants by cuttings is described as follows:

Step 1: Soaking of rockwool cubes (4.0×4.0×4.0 cm) in fertilizers with an EC value of 1.4±0.2 mS/cm and a pH value of 5.5-6.5 including nematodes (*Steinernema feltiae*) for a minimum of 10 minutes.

Step 2: Taking a cutting of approximately 8-12 cm and 2-3 unfolded leaves of the motherplant.

Step 3: Removing of lower leaves of the cutting.

Step 4: Cutting the stem at the lower end with an angle of 45 degrees.

Step 5: Cutting in half the upper large leaves.

Step 6: Removing the uppermost layer (approximately 2 mm) of the stem of the lower 2 cm of the step.

Step 7: Sticking of cutting in the prepared rockwool cubes with a depth of approximately 1.5-2 cm.

Step 8: Placing of the cutting sticking in the rockwool cubed under a white plastic foil tent.

Step 9: Spray the cutting with water to increase the humidity under the with plastic foil tent.

Step 10: After day 1 the white plastic foil tent is cut open at the top with holes of approximately 5 cm (1 hole for every $m^2$).

Step 11: In day 3-9 the cuttings are supplied with fertilizer for 15 min (EC 1.4±0.2 mS/cm) by flooding the cultivation table.

Step 12: On day 9±2 further holes are cut in the white plastic tent, approximately 5 cm (5 holes for every $m^2$).

Step 13: Between day 10-13 cuttings are supplied with fertilizer for 15 min (EC 1.6±0.2 mS/cm) by flooding the cultivation table.

Step 14: On day 11±2 the white plastic tent is removed for 15-60 min/day.

Step 15: On day 14 until Vegetative Phase the cuttings are supplied with fertilizer for 15 min (EC 1.8±0.2 mS/cm by flooding the cultivation table. In addition, the white plastic tent is replaced with acryl mesh for 1-2 days.

Step 16: For the days until Vegetative Phase (approximately day 21) cuttings are uncovered in greenhouse.

Step 17: Preparation of rockwool cubes for Vegetative Phase (15×15×14.2 cm) with the insertion of two to three drippers in each rockwool cube by an 45° angle into the cube.

Step 18: Soaking of the rockwool cubes in fertilizer with EC of 2.2-2.8 mS/cm and a pH value 5.5-6.5 by fertilizer from the installed drippers for 20±5 seconds for 20±5 times, with a 5 min break in between.

Step 19: Soaking of rockwool cubes with fertilizer containing nematodes (*Steinernema feltiae*) from drippers.

Step 20: Transition from Rooting phase (approx. 21 days) to Vegetative Phase (approx. 14 days).

Step 21: Transplantation of cutting in rockwool cubes for Vegetative Phase.

Step 22: Plants are kept under the same conditions for their lifetime of about 8 to 12 months with fertilizer of 2.2-2.8 mS/cm and a pH value 5.5-6.5.

The detailed steps of cultivation of production plants by cuttings is described as follows:

Step 1: Soaking of rockwool cubes (4.0×4.0×4.0 cm) in fertilizers with an EC value of 1.4±0.2 mS/cm and a pH value of 5.5-6.5 including nematodes (*Steinernema feltiae*) for a minimum of 10 minutes.

Step 2: Taking a cutting of approximately 8-12 cm and 2-3 unfolded leaves of the motherplant.

Step 3: Removing of lower leaves of the cutting.

Step 4: Cutting the stem at the lower end with an angle of 45 degrees.

Step 5: Cutting in half the upper large leaves.

Step 6: Removing the uppermost layer (approximately 2 mm) of the stem of the lower 2 cm of the step.

Step 7: Sticking of cutting in the prepared rockwool cubes with a depth of approximately 1.5-2 cm.

Step 8: Placing of the cutting sticking in the rockwool cubed under a white plastic foil tent.

Step 9: Spray the cutting with water to increase the humidity under the with plastic foil tent.

Step 10: After day 1 the white plastic foil tent is cut open at the top with holes of approximately 5 cm (1 hole for every $m^2$).

Step 11: In day 3-9 the cuttings are supplied with fertilizer for 15 min (EC 1.4±0.2 mS/cm) by flooding the cultivation table.

Step 12: On day 9±2 further holes are cut in the white plastic tent, approximately 5 cm (5 holes for every $m^2$).

Step 13: Between day 10-13 cuttings are supplied with fertilizer for 15 min (EC 1.6±0.2 mS/cm) by flooding the cultivation table.

Step 14: On day 11±2 the white plastic tent is removed for 15-60 min/day.

Step 15: On day 14 until Vegetative Phase the cuttings are supplied with fertilizer for 15 min (EC 1.8±0.2 mS/cm by flooding the cultivation table. In addition, the white plastic tent is replaced with acryl mesh for 1-2 days.

Step 16: For the days until Vegetative Phase (approximately day 21) cuttings are uncovered in greenhouse.

Step 17: Preparation of rockwool cubes for Vegetative Phase (15×15×14.2 cm) with the insertion of two to three drippers in each rockwool cube by an 45° angle into the cube.

Step 18: Soaking of the rockwool cubes in fertilizer with EC of 2.2-2.8 mS/cm and a pH value 5.5-6.5 by fertilizer from the installed drippers for 20±5 seconds for 20±5 times, with a 5 min break in between.

Step 19: Soaking of rockwool cubes with fertilizer containing nematodes (*Steinernema feltiae*) from drippers.

Step 20: Transition from Rooting phase (approx. 21 days) to Vegetative Phase (approx. 14 days)

Step 21: Transplantation of cutting in rockwool cubes for Vegetative Phase.

Step 22: Until flowering phase plants are supplied with fertilizer for 2±1,5 min with an EC value of 2.4±0.2 mS/cm for every day by drippers.

Step 23: Plants are topped after day 7±2 days in Vegetative Phase by cutting the top above 4/6 branches Step 24: Transition from Vegetative Phase (approx. 14 days) to Flowering phase (approx. 9 weeks)

Step 25: Flowering phase is initiated by changing the daylight from 18 h/day to 12 h/day.

Step 26: The plants are supplied with fertilizer during the Flowering phase every day for 3±1 times for 2±1.5 min with EC of 2.2-30 mS/cm.

Step 27: After 10±5 days in flowering removing of all shoots and leaves in the lower half of the plant by directly cutting on the side shoot Step 28: Remaining flowering phase of approx. 9 weeks Executing of pest inspection every day in all phases, spreading of beneficials as needed (*Nematodes, Hypoaspis, Atheta, Orius, Aphidius Colemani, Cucumeris, Californicus, Swirskii, Felitiella acarisuja*)

Asexual Reproduction.

'DKJ127' has been propagated as vegetative stem cuttings since its original selection. The first propagation of 'DKJ127' took place on Aug. 1, 2019 at Vertanical Denmark ApS, Birketvedvejen 31, 5290 Marslev, Denmark. The characteristics disclosed herein for 'DKJ127' have remained stable and the plant has reproduced true to type through successive generations of asexual propagation.

SUMMARY OF THE INVENTION

'DK-J12' is a high THC producing *Cannabis* cultivar. "DKJ127" represents a significant improvement over existing *Cannabis* strains in terms of its unique cannabinoid profile and high yield. The inventive step lies in the discovery of a specific combination of genetic traits that result in the desirable characteristics of the strain.

'DKJ127' exhibits a high to very high THC content, about 17-20% THC eq. and absent to low CBD content, about 0.07% CBD eq., which characteristic reproduces true to type through successive generations of asexual propagation and distinguishes 'DKJ127' as a new and distinct *Cannabis* cultivar.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Cannabis sativa* variety 'DKJ127'. As used herein, the term "variety" is interchangeable with the terms "cultivar," "line" and/or "strain."

FIG. 4A shows a 5-month-old plant and FIG. 4B shows a 7-month-old plant.

DETAILED BOTANICAL DESCRIPTION

Figure 1:
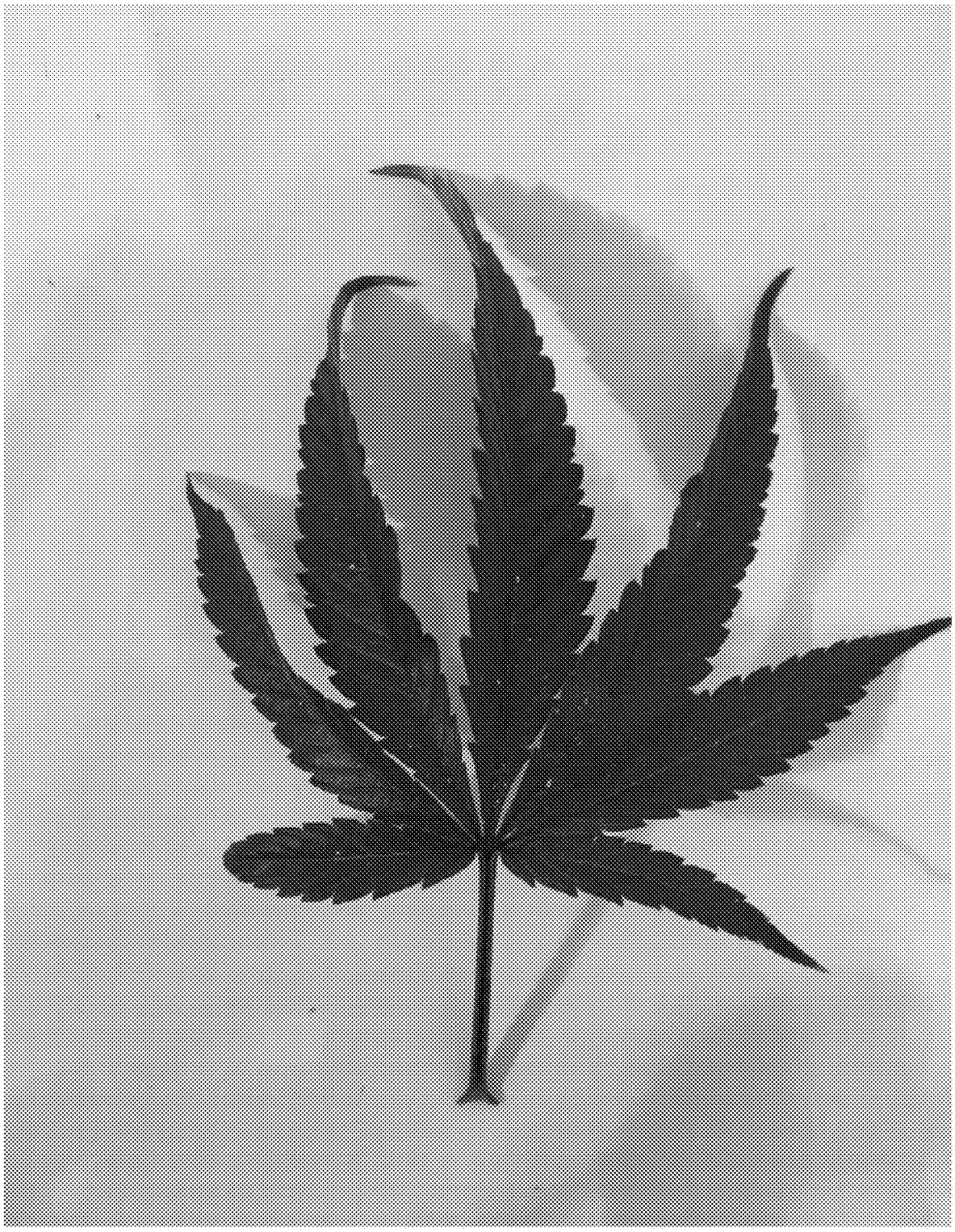
FIG. 1 is a color photograph of a leaflet of the new cultivar 'DKJ127'.
Figure 2:
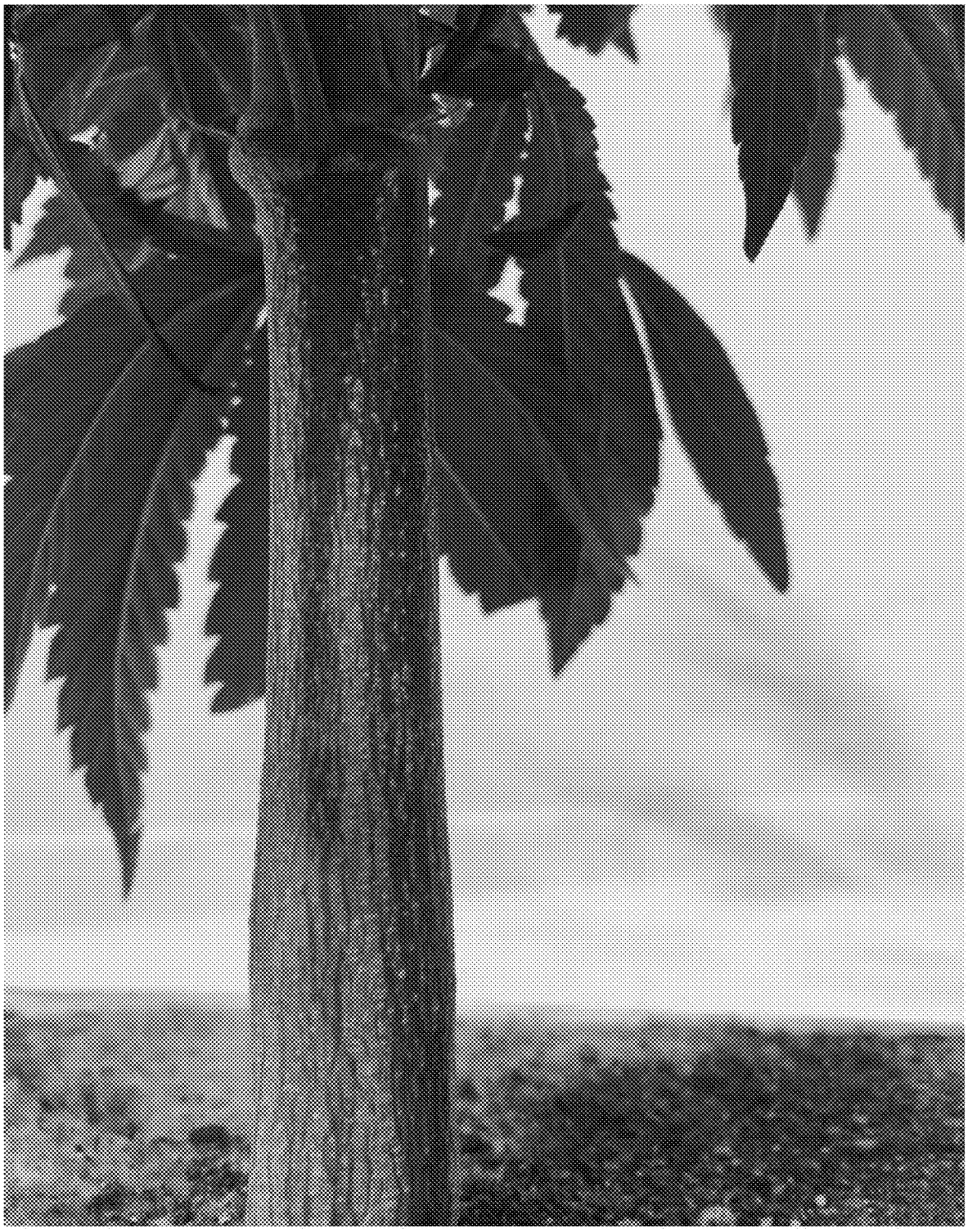
FIG. 2 is a color photograph of a stem of the new cultivar 'DKJ127'.
Figure 3:
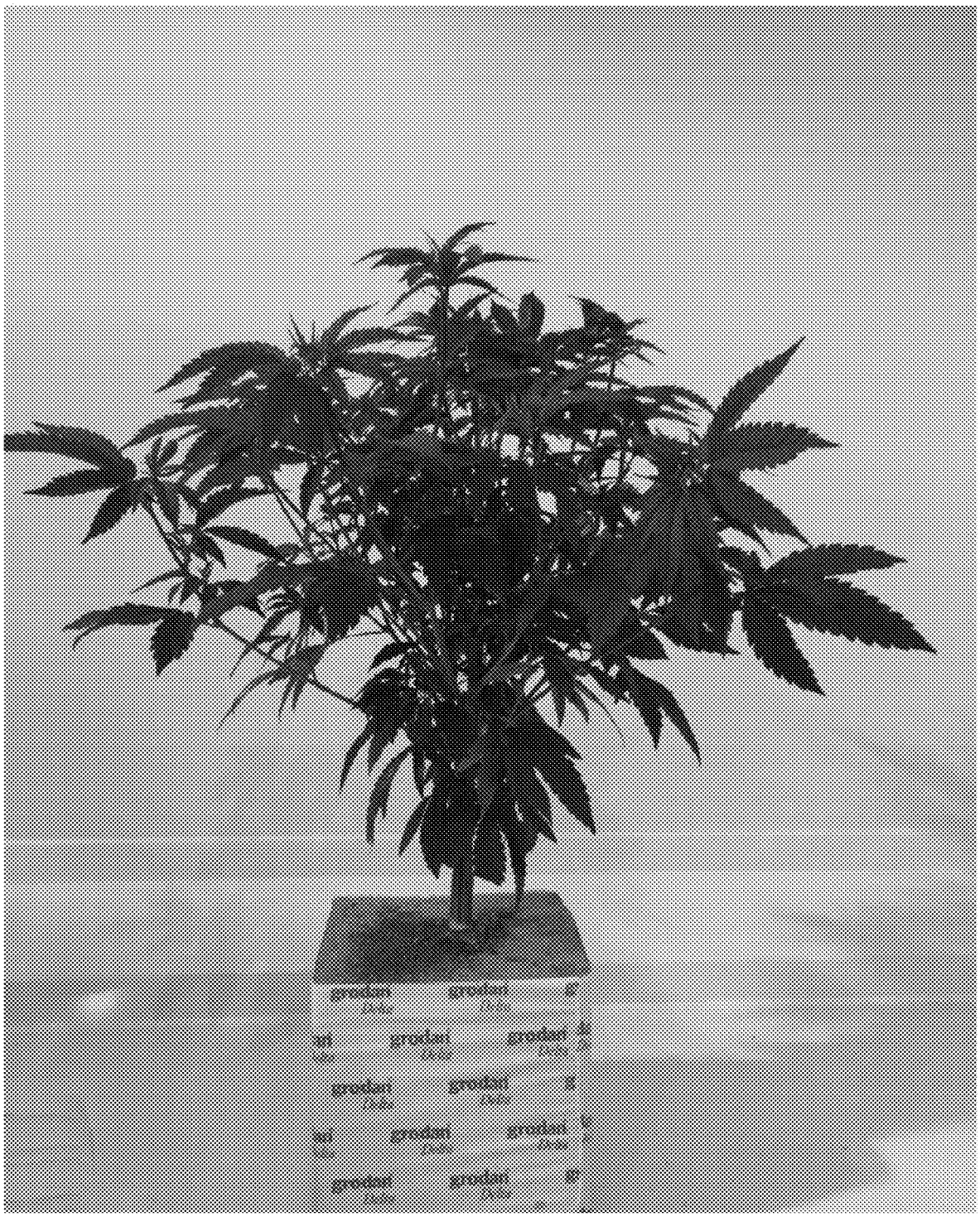
FIG. 3 is a color photograph of a plant of the new cultivar 'DKJ127'.
Figure 4A:
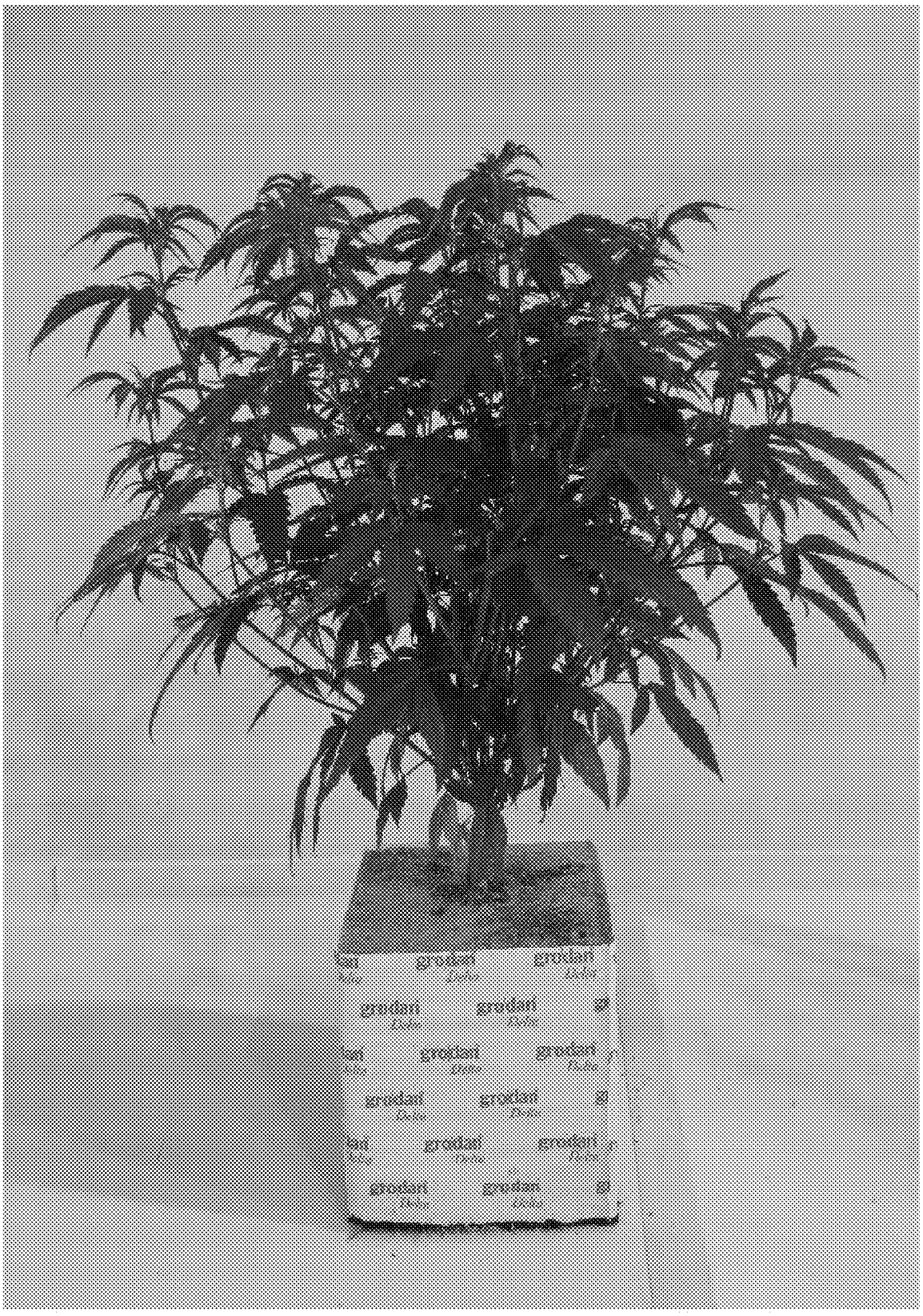
FIGS. 4A and 4B show color photographs of the new cultivar 'DKJ127' at different stages of growth.
Figure 4B:
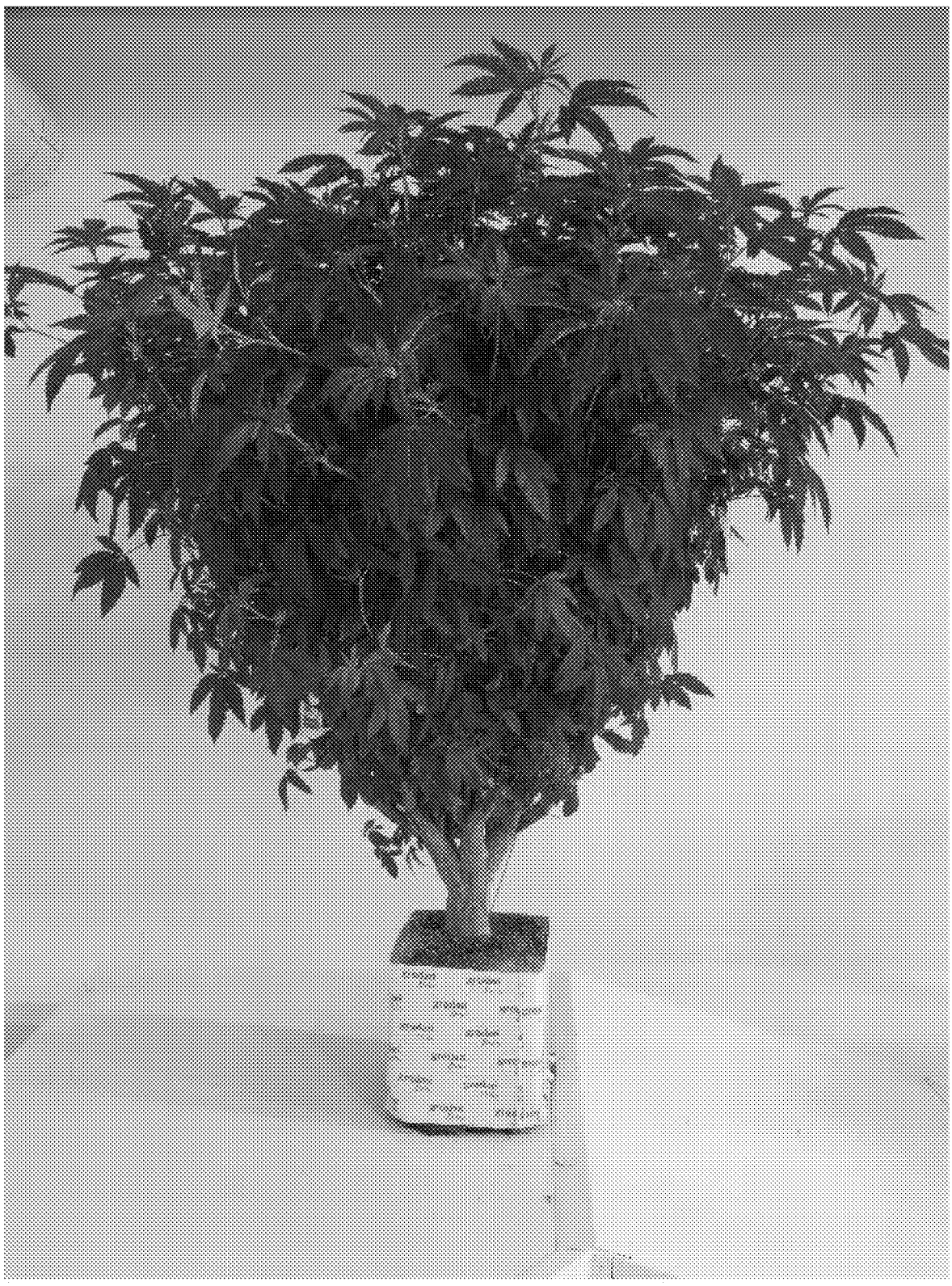

The following is a detailed description of the botanical characteristics of a new and distinct cultivar of *Cannabis sativa* plant given the designation 'DKJ127'. All colors cited herein refer to The Royal Horticultural Society Colour Chart (The Royal Horticultural Society (R.H.S.), London, 2007 Edition). Where dimensions, sizes, colors, and other characteristics are given, it is to be understood that such characteristics are approximations or averages set forth as accurately as practicable.

'DKJ127' has not been observed under all possible environmental conditions; therefore, the phenotype may vary under different environmental conditions such as season, temperature, light intensity, day length, cultural conditions, and the like, without, however, any variance in the genotype.

TECHNICAL DESCRIPTION OF THE CULTIVAR

Classification.

*Botanical name.*—*Cannabis saliva* (L.).

*Common name.*—*Cannabis.*

*Variety name.*—'DKJ127'.

Parentage: Seedling selection grown from 'Jack Herer' seed.

Propagation: Typically propagated asexually via stem cuttings.

Plant description:

*Plant height.*—Medium; about 140 cm-150 cm by the end of flowering.

Main stem:

*Shape.*—Strong, erect, woody and coarse. It varies in thickness, thicker in the bottom, and narrower in the top.

*Average diameter at the bottom.*—1.8-2.5 cm.

*Average diameter.*—1 cm.

*Average internodal length.*—4 cm.

*Furrow depth.*—Shallow.

*Amount of pith in cross-section.*—Absent.

*Thrycome type.*—No trichomes on stem.

*Color designation.*—Green (close to RHS 140 A), with violet stripes (close to RHS 86A), and grey tones at the bottom (close to RHS 139 D).

Foliage:

*Leaf description.*—Arrangement: serrate leaflets arranged alternately on the stems. Size: Length: fluctuates from 5 cm to 23 cm, depending by age and position (without petiole). Width: fluctuates from 6 cm to 15 cm depending by age and position (without petiole). Margin: coarsely serrate. Trichomes type: non-glandular, cystolithic. Leaflet shape: broad. Leaflet size (Length and width in cm): 5 cm-23 cm, similar to 'Dioca 88'. Average number of leaflets per leaf: 5, similar to 'Epsilon 68'. Leaf tip: pointed. Base shapes: obtuse. Color designations of the leaf veins (top surface): light green (close to RHS 142 D). Color designations of the leaf veins (bottom surface): light green (close to RHS 142 D). Color specification of the top surface: dark green: (close to RHS 141B). Color specification of the bottom surface: green (close to RHS 139A).

*Petiole description.*—Length: fluctuates, from 3 cm to 15 cm, depending by the age of the leaf and position on the plant (bottom, mid or top). Anthocyanin staining: medium purple coloration (close to RHS N77B). Thrycome type: cystolithic trichomes. Coloring: green (close to RHS: 145A).

Flower description: The average diameter of DKJ127 flower is 4 cm at the end of week 9 in flowering phase. It is not possible to directly compare the flower size with the genetic "Jack Herer" as the genetic "Jack Herer" displays various phenotypes with different flower sizes.

*Timing of female flowering.*—Early to medium. Female flowering starts approximately 14 days after beginning of the flowering induction. Induction starts by changing the daylength from 18 to 12 hours.

*Period of flowering.*—About 9 weeks.

Figure 11:
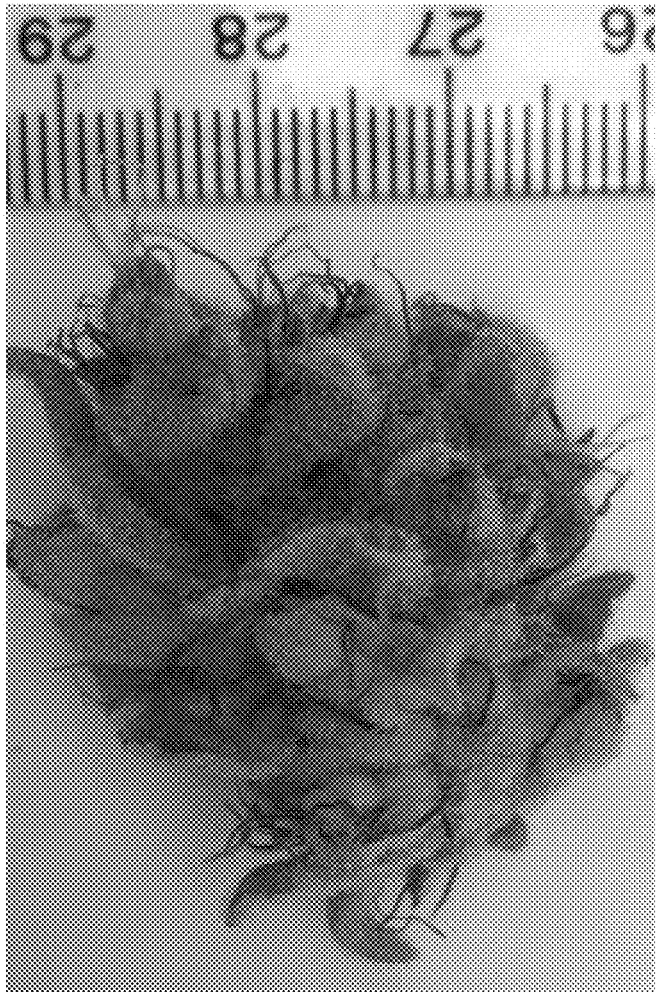
FIG. 11 shows a bottom flower of 'DKJ127'.
Figure 12:
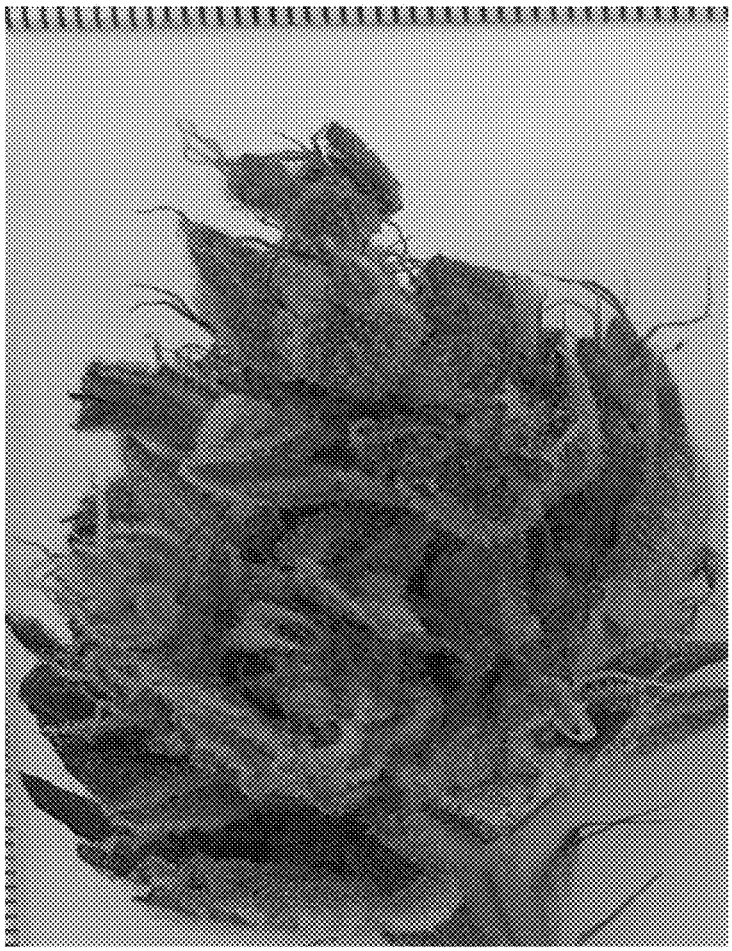
FIG. 12 shows a middle flower of 'DKJ127'.
Figure 13:
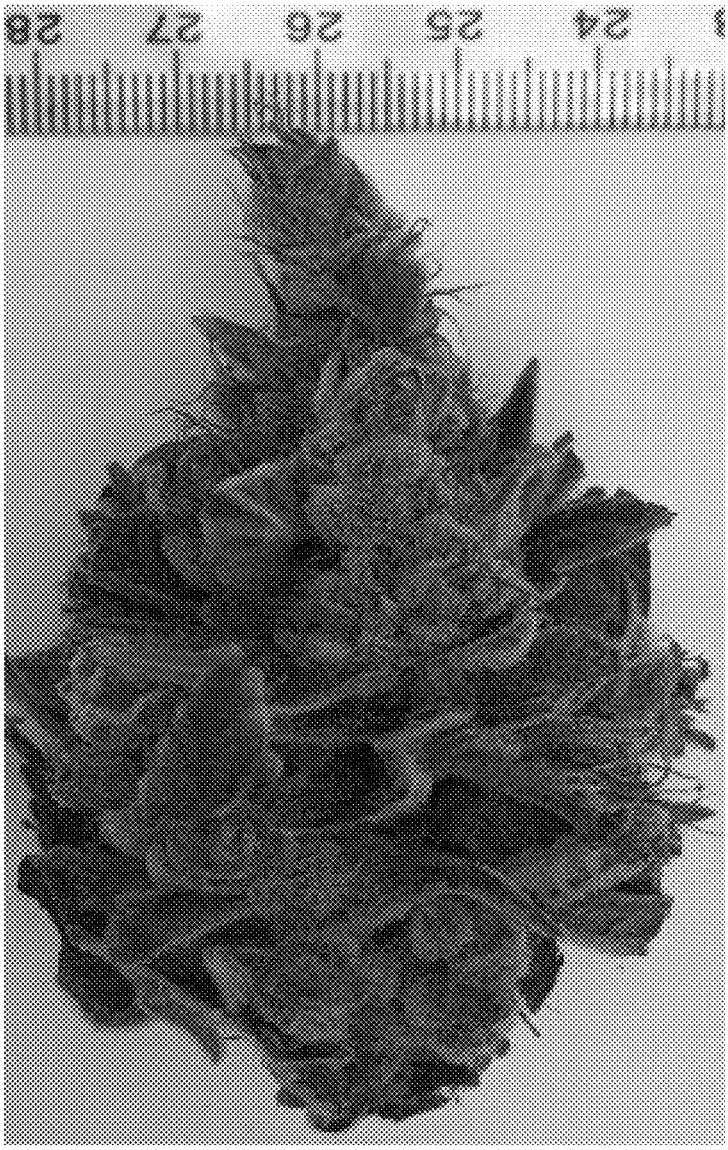
FIG. 13 shows a top flower of 'DKJ127'.

*Color.*—Dark to bright green, sometimes purple on the upper part (RHS: 143A and RHS: 141B). Bottom flowers are smaller, since they are exposed to lower light intensity than flowers located higher up in the plant. The average diameter is 3 cm. See, FIG. 11. Middle flowers are bigger than bottom flowers, since they are exposed to higher light intensity. The average diameter is 4 cm. See, FIG. 12. Top flowers are bigger than the flowers located in the middle or at the bottom of the plant, since they are exposed to higher light intensity- The average diameter is 5 cm. See, FIG. 13.

Inflorescence: Is formed by arrangement of individual flowers located around a stem. The stem of the inflorescence is thick and sturdy, and it supports the weight of the flowers. Each flower is enclosed in a small, cone-shaped structure.

*Pistils are in the center of each flower.*—All flowers are covered with glandular, capitate-stalked trichomes. The inflorescence is surrounded by sugar-leaves (bracts).

*Average number of inflorescences per plant.*—110.

*Average number of flowers per inflorescence.*—30. DK-J127 develop male flowers at the beginning of week 8 in flowering phase.

*Female flowers per plant.*—99.998%.

*Male flowers per plant.*—0.002%.

*Hermaphrodite per plant.*—0%.

*Average number of flowers per inflorescence.*—3.

*Average inflorescence diameter.*—4 cm.

*Terminal bud shape.*—Dense, tightly packed, oval shaped, green color (close to RHS 143A).

Bract:

*Average size.*—5 mm.

*Shape.*—Small, pear-shaped.

*Trichome type.*—Glandular, capitate stalked.

*Color.*—Green (close to RHS 143A).

Bracteole:

*Average size.*—2 cm.

*Shape.*—Tiny leaves, coarsely serrate, covered with trichomes.

*Trichome type.*—Glandular, capitate stalked.

*Color.*—Green (close to RHS: 141A).

Productivity (weight/plant), shipping quality and storage life: DKJ127 is used as a starting product for the product VER-01-THC (dry *Cannabis* flowers), which is used for ethanolic extraction. Yield of dried *Cannabis* flowers/plant is approximately 60-80 gr. Storage conditions 15-25° C. Shelf-life 2 years.

Plant hardiness zone: Hardiness zone 11 with a range between 40° F. and 50° F. or +4.4° C. and +10° C.

Chemical content:

*THC and CBD content.*—About 17-20% THC eq. and about 0.07% CBD eq.

Figure 5:
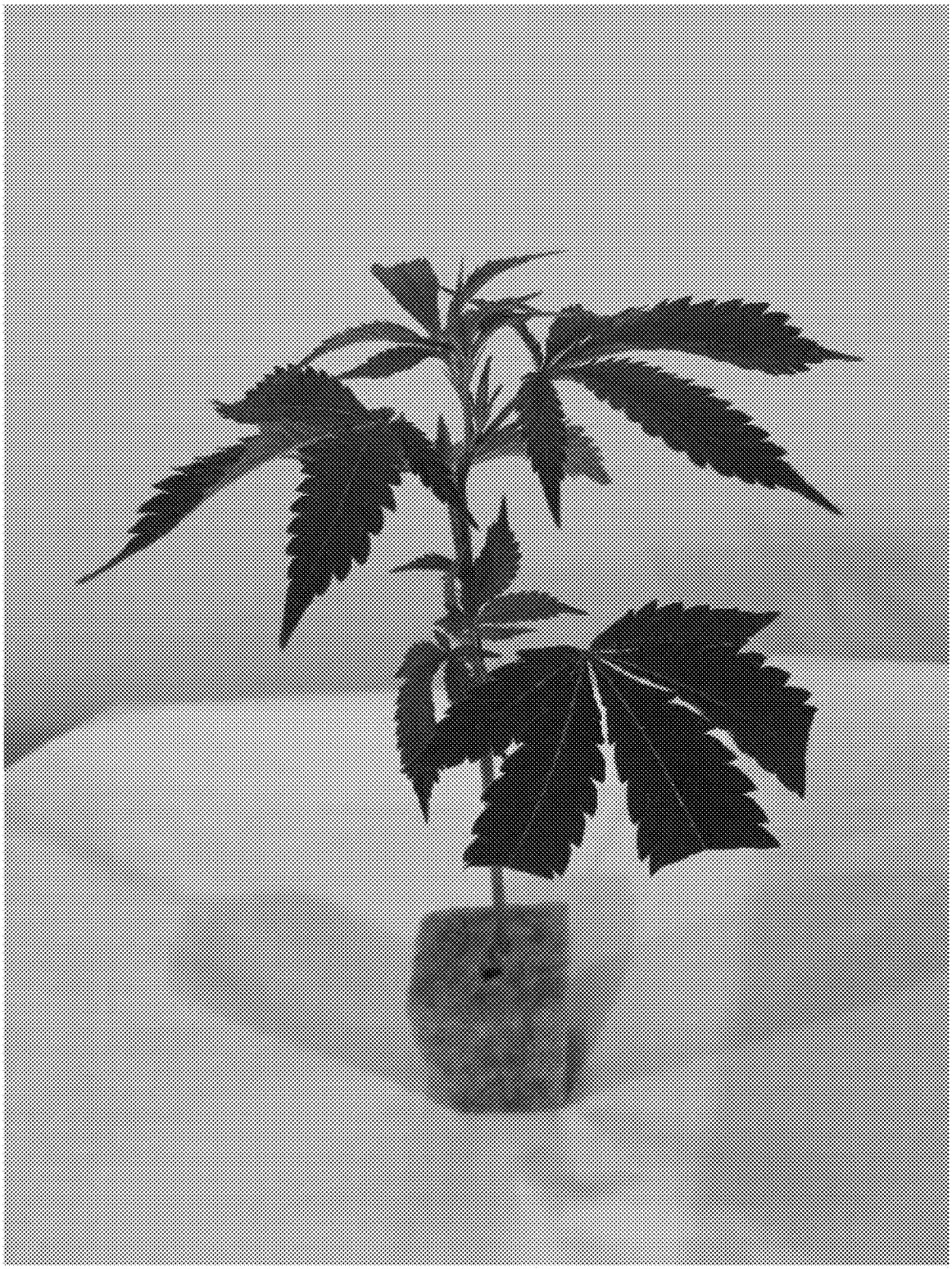
FIG. 5 is a color photograph of a cutting of the new cultivar 'DKJ127', which is 1.5 weeks old.
Figure 6:
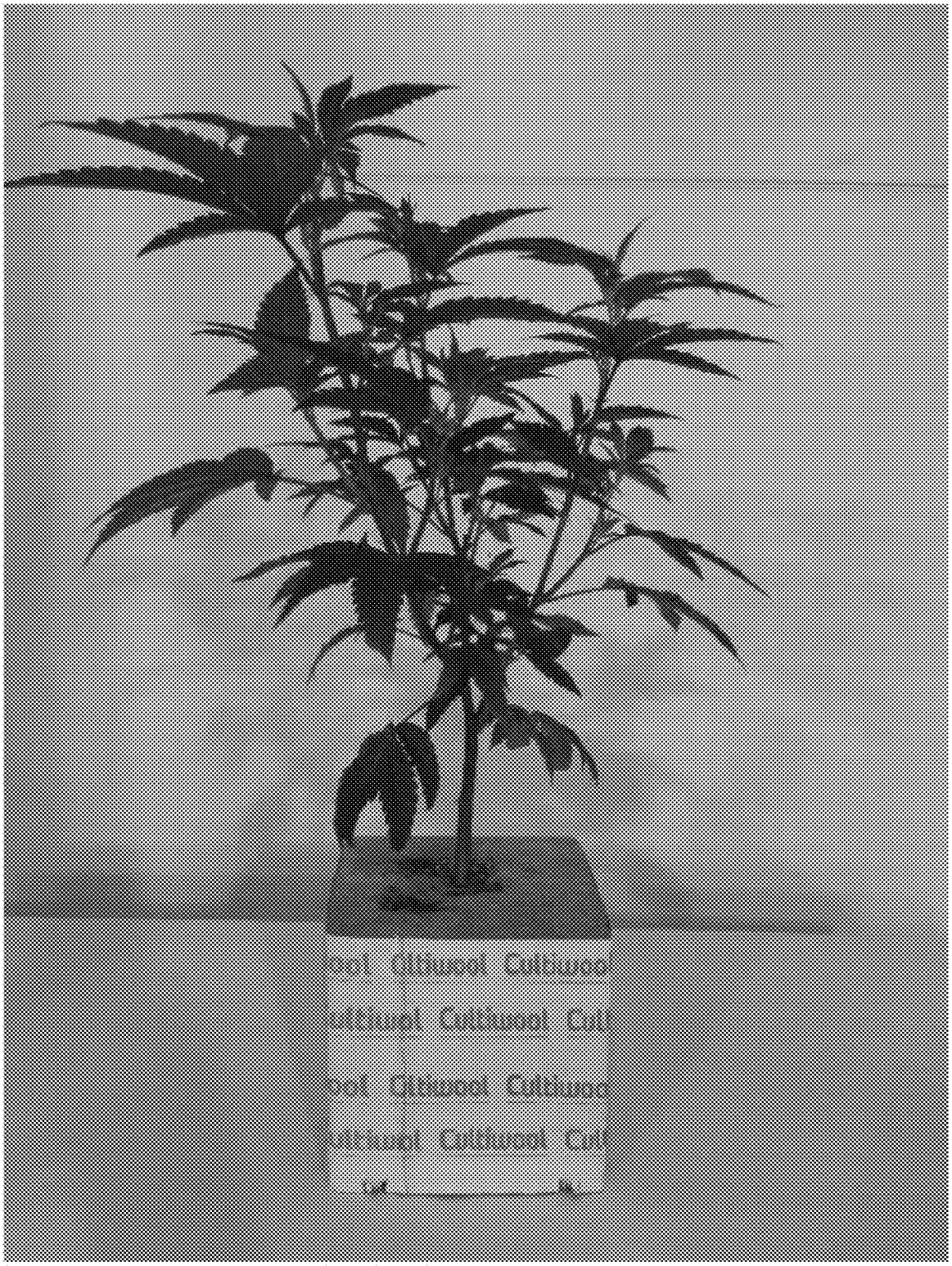
FIG. 6 is a color photograph of a plant of the new cultivar 'DKJ127' in the vegetative stage that is 4.5 weeks old.
Figure 7:
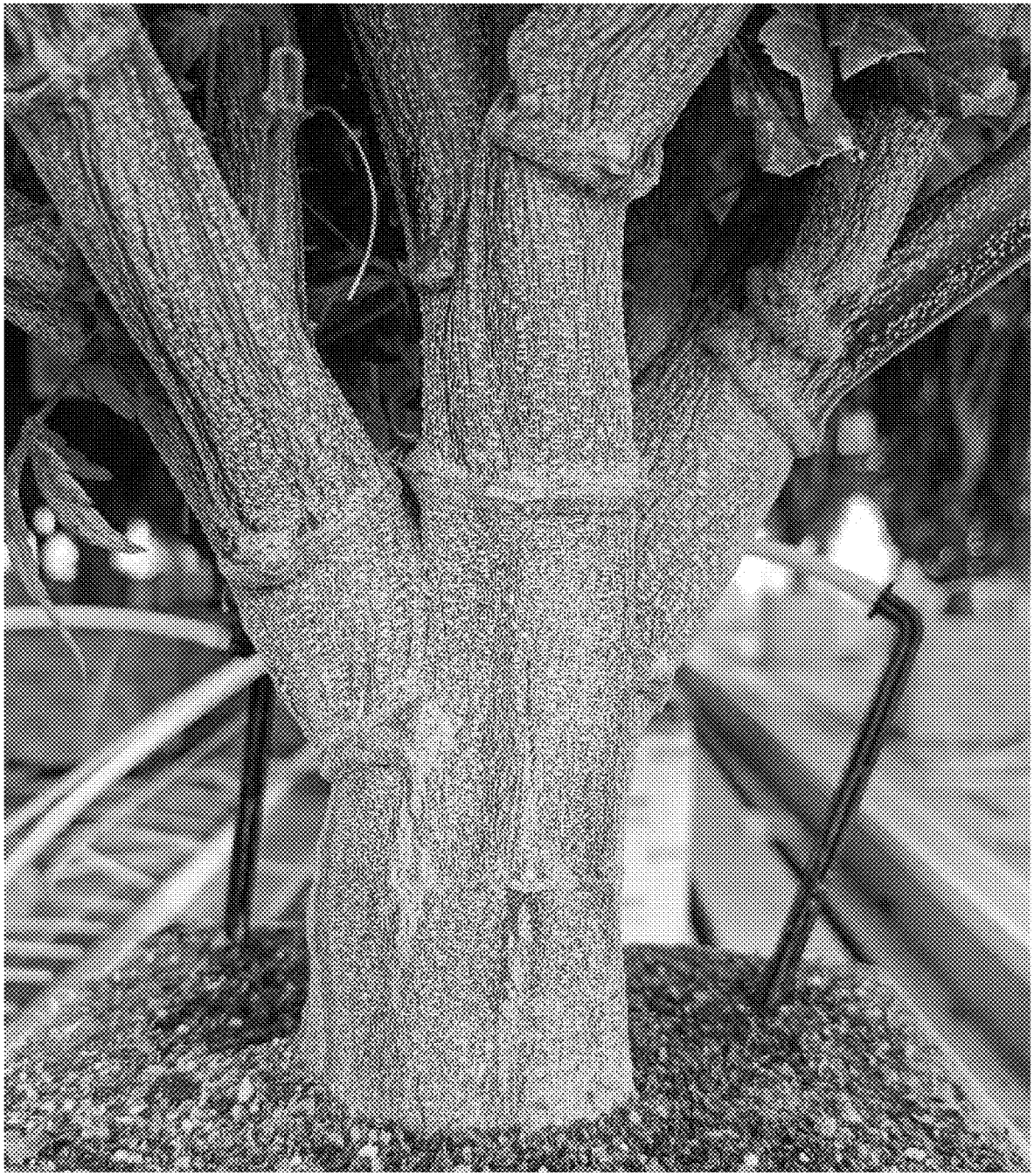
FIG. 7 is a color photograph of the stem of a plant of the new cultivar 'DKJ127' that is 7 months old.
Figure 8:
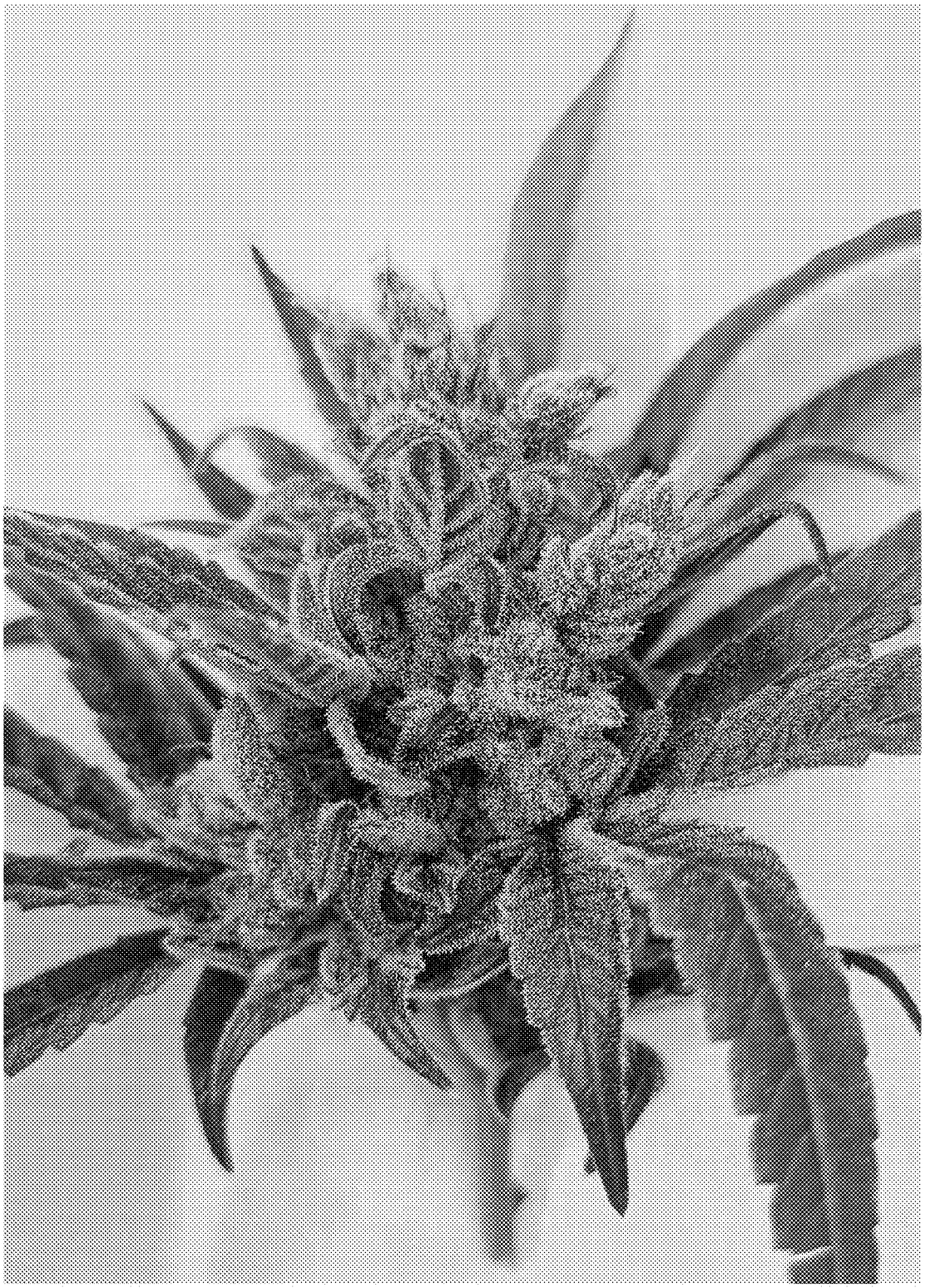
FIG. 8 and FIG. 9 are a color photographs of the flower of a plant of the new cultivar 'DKJ127'.
Figure 9:
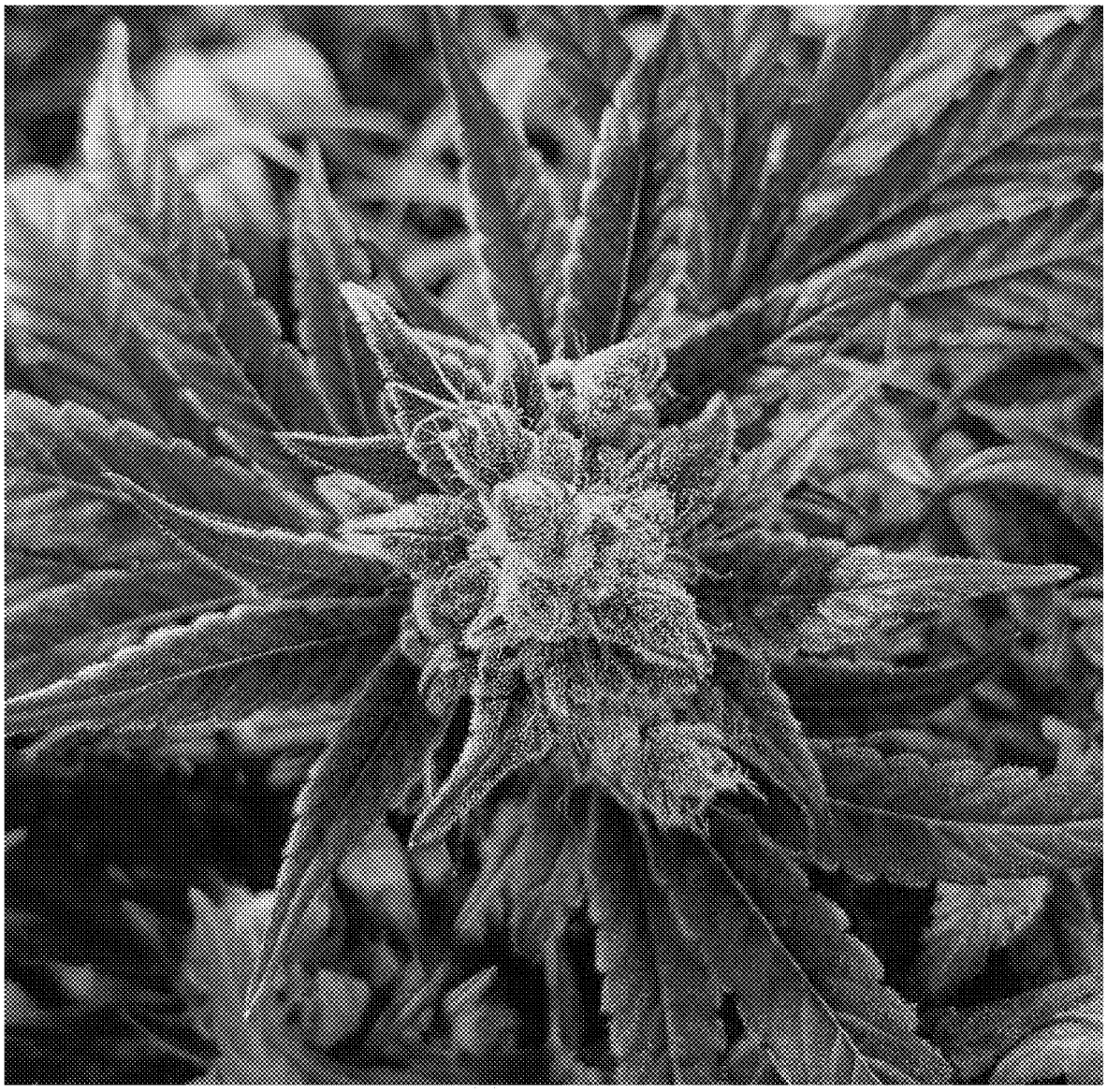
Figure 10:
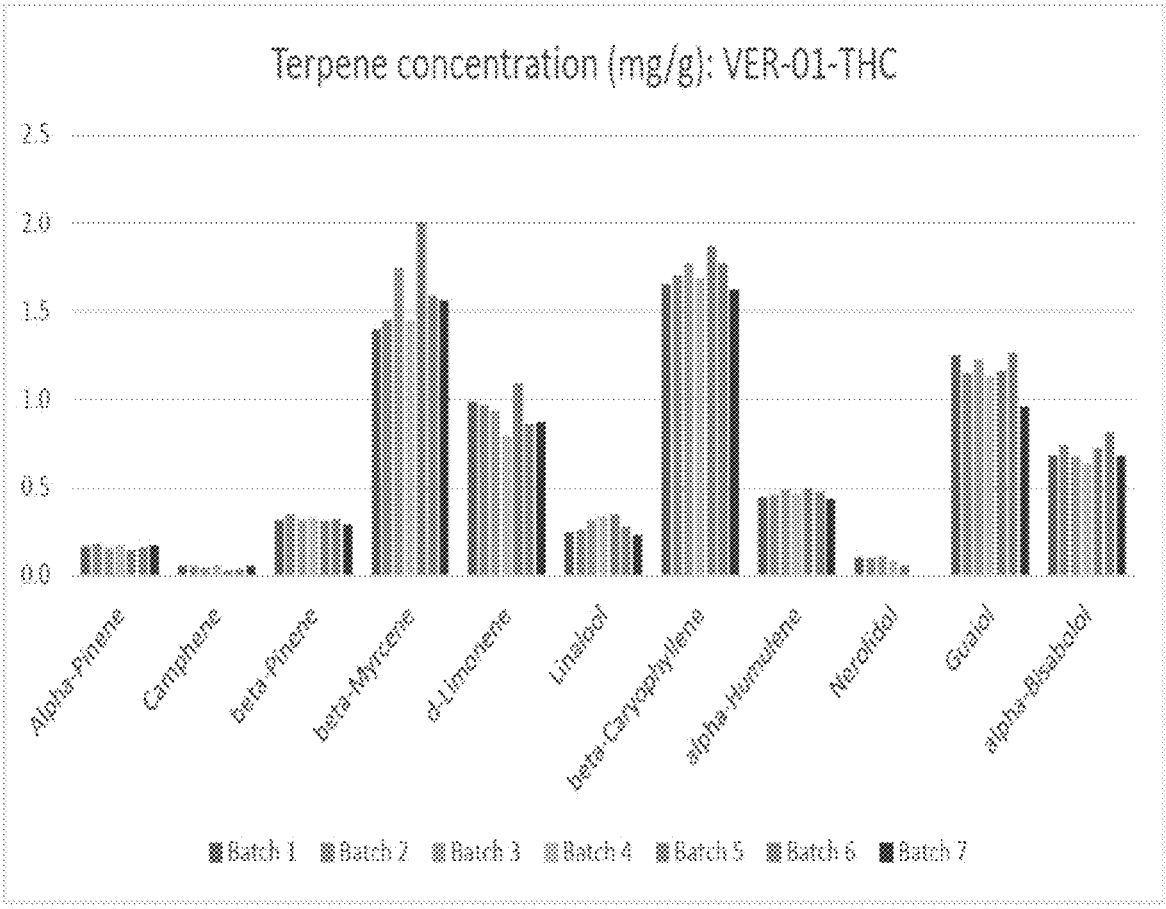
FIG. 10 shows the concentrations of various terpenes from different batches of 'DKJ127'. 'VER-01-THC' is the commercial name for 'DKJ127'.

*Terpene content.*—DKJ127 produces alpha-pinene, camphene, beta-pinene, beta-myrcene, d-limonene, linalool, beta-caryophyllene, alpha-humulene, nerolidol, guaiol, and alpha-bisabolol. See, FIG. 5.

COMPARISON TO 'JACK HERER'

'DKJ127' has a consistently higher THC content than 'Jack Herer', about 17-20% THC eq.

I claim:

1. A new and distinct cultivar of *Cannabis sativa* plant named 'DKJ127', substantially as illustrated and described herein.

* * * * *